(12) United States Patent
Yoo et al.

(10) Patent No.: US 8,557,793 B2
(45) Date of Patent: Oct. 15, 2013

(54) THEANINE DERIVATIVE, PREPARATION METHOD THEREOF, AND USE THEREOF FOR ALLEVIATING ACNE

(75) Inventors: Jae Won Yoo, Yongin-si (KR); Yu Na Yun, Yongin-si (KR); Seo Young Kim, Yongin-si (KR); Jin Young Lee, Yongin-si (KR); Jun Oh Kim, Yongin-si (KR); Jun Cheol Cho, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 13/816,124

(22) PCT Filed: Aug. 9, 2011

(86) PCT No.: PCT/KR2011/005788
§ 371 (c)(1),
(2), (4) Date: Feb. 8, 2013

(87) PCT Pub. No.: WO2012/020966
PCT Pub. Date: Feb. 16, 2012

(65) Prior Publication Data
US 2013/0137653 A1    May 30, 2013

(30) Foreign Application Priority Data
Aug. 11, 2010   (KR) .................. 10-2010-0077209

(51) Int. Cl.
*A61K 31/715* (2006.01)
*A61K 31/12* (2006.01)
*C13K 5/00* (2006.01)

(52) U.S. Cl.
USPC .................... 514/53; 514/676; 536/123.13

(58) Field of Classification Search
None
See application file for complete search history.

(56) References Cited

U.S. PATENT DOCUMENTS

| | | |
|---|---|---|
| 6,831,103 B1 | 12/2004 | Ueda et al. |
| 2008/0009505 A1 | 1/2008 | Hodges et al. |
| 2010/0254969 A1 | 10/2010 | Baik et al. |

FOREIGN PATENT DOCUMENTS

| | | |
|---|---|---|
| JP | 2005-247700 A | 9/2005 |
| KR | 10-0704523 B1 | 4/2007 |
| KR | 10-0793825 B1 | 1/2008 |

*Primary Examiner* — Traviss C McIntosh, III
(74) *Attorney, Agent, or Firm* — Sughrue Mion, PLLC

(57) ABSTRACT

The present invention relates to a theanine derivative, a preparation method thereof, and a use thereof for anti-acne treatment, having a selective inhibitory effect on *Propionibacterium acnes* in the skin.

10 Claims, No Drawings

THEANINE DERIVATIVE, PREPARATION METHOD THEREOF, AND USE THEREOF FOR ALLEVIATING ACNE

TECHNICAL FIELD

The present invention relates to a theanine derivative, a preparation method thereof, and a use thereof for anti-acne treatment, where the theanine derivative is represented by the following formula 1 or 2 and having a selective inhibitory effect on *Propionibacterium acnes* in the skin:

[Formula 1]

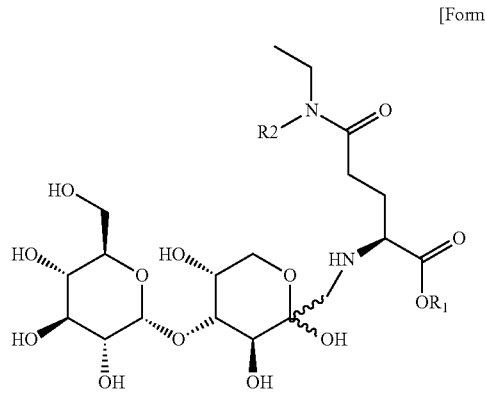

(In the formula, $R_1$ and $R_2$ are hydrogen, methyl, ethyl, propyl, isopropyl, n-butyl, isobutyl, or t-butyl),

[Formula 2]

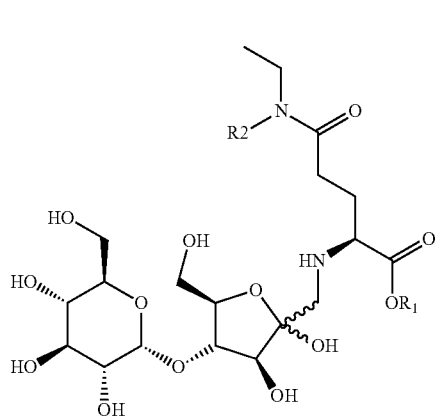

(In the formula, $R_1$ and $R_2$ are hydrogen, methyl, ethyl, propyl, isopropyl, n-butyl, isobutyl, or t-butyl).

BACKGROUND ART

Green tea is an herbal beverage that stands out as a favorite drink in many Asian countries and has recently taken a spotlight all over the world as its several efficacies in the human body have proven. Green tea is known to contain a variety of ingredients, such as polyphenols, protein amino acids, vitamins, minerals, and so forth. Among these ingredients of green tea, polyphenols, particularly epigallocatechin gallate (EGCG), known to have strong anti-oxidant and anti-cancer effects have been the subject of a number of studies.

However, there is a growing interest in theanine, an amino acid specifically abundant in *Camellia sinensis*, since theanine has proved as an ingredient that is a major determinant in providing the savor and efficacy of green tea. Theanine is biosynthetically produced through an enzyme reaction of glutamine and ethylamine in the root of *Camellia sinensis*, transferred to the leaves and concentrated. Theanine in the leaves is partly converted to polyphenols by the sun light but mostly exists in the form of free amino acids, the amount of which is known to be 1 to 2% of the total dry weight of the leaves, taking over 50% of the total amino acids. The studies on the efficacy of theanine have been made focusing on the benefits of theanine related to the nerve system, such as it promotes Alpha wave generation in the drain, a sign of induced relaxation, reduces physical and mental stress, and protects nerve cells. Recently, it has been reported that theanine has efficacy in skin moisturization and promotion of collagen biosynthesis through activation of prolidase, but the studies on the efficacy of theanine in the skin are not entirely satisfactory. Like this, many studies are being made on the theanine derivatives as well as theanine, such as the theanine derivative with enhanced stability (U.S. Patent Application Pub. No. 2008/0009505) as the benefits of theanine in the skin have been demonstrated.

In this context, the inventors of the present invention have been studying on theanine and its derivatives and growing more interested in the theanine derivatives bound to sugar. There are a variety of methods of introducing a sugar into a theanine derivative, most of which have some problems, such as necessity of involving complicated steps of introducing and removing a protective group. But, the use of the Amadori rearrangement reaction enables introduction of a sugar into a theanine derivative without carrying out the complicated steps, such as of adding a protective group. However, the progress of the Amadori rearrangement reaction leads to conversion of a desired product into a different substance and increased yield of by-products, consequently with the difficulty in obtaining a desired product at high yield.

For the reason, the methods use more sugars than needed in the actual reaction and need to isolate a desired product using an ion-exchange resin after the reaction, which is uneconomical and unsuitable for large-scale production. Furthermore, the desired product in many cases possibly has deterioration in color by the effect of by-products. Accordingly, there is a need for improving those problems.

On the other hand, different kinds of bacteria form a specific colony in the skin and play a role as a primary barrier protecting against external microorganisms entering the human body. It is however known that an abnormal proliferation of bacteria harmful to the skin causes skin problems, where the representative one of such bacteria is *Propionibacterium acnes* (*P. acnes*) known to cause acnes in the skin. There have been made attempts to find out a substance that has a selective anti-bacterial effect on *Propionibacterium acnes* without affecting other bacteria existing in the skin but insignificantly harmful to the skin. Theanine is known to have an anti-bacterial effect, which is insignificant. Thus, there is a need for improved effects of theanine for the sake of the practical use of theanine.

DISCLOSURE OF INVENTION

Technical Problem

In an attempt to study theanine derivatives having skin-related efficacies, the inventors of the present invention have found out that a theanine derivative of a specific structure has a selective anti-bacterial effect on *Propionibacterium acnes*, thereby completing the present invention.

It is therefore an object of the present invention to provide a theanine derivative and its use for anti-acne treatment, which theanine derivative is to have a selective anti-bacterial effect on *Propionibacterium acnes*.

It is another object of the present invention to provide a method for preparing the theanine derivative.

Technical Solution

To accomplish the above objects, the present invention is to provide a theanine derivative and its use for anti-acne treatment, where the theanine derivative is represented by the following formula 1 or 2:

[Formula 1]

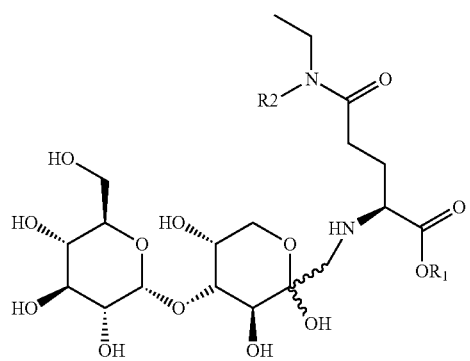

(In the formula, $R_1$ and $R_2$ are hydrogen, methyl, ethyl, propyl, isopropyl, n-butyl, isobutyl, or t-butyl),

[Formula 2]

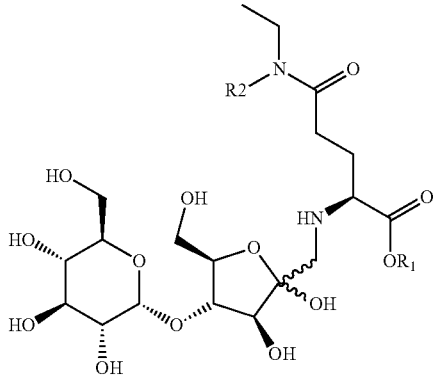

(In the formula, $R_1$ and $R_2$ are hydrogen, methyl, ethyl, propyl, isopropyl, n-butyl, isobutyl, or t-butyl).

The present invention is also to provide a method for preparing a theanine derivative represented by formula 1 or 2 as shown in the following reaction scheme 1:

Reaction Scheme 1

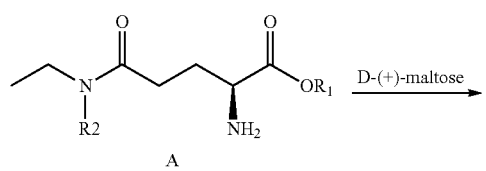

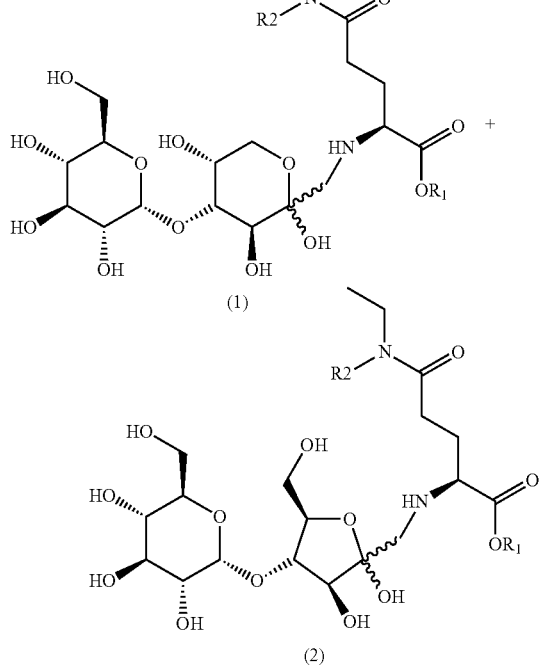

wherein $R_1$ and $R_2$ are hydrogen, methyl, ethyl, propyl, isopropyl, n-butyl, isobutyl, or t-butyl, where the method comprises: heating compound A and maltose in a reaction solvent under agitation to activate a reaction; and precipitating a product in the reaction solvent.

Advantageous Effects

The theanine derivative of the present invention has a good selective anti-bacterial effect on *Propionibacterium acnes* without affecting other bacteria existing in the skin but insignificantly harmful to the skin. Further, the preparation method of the present invention provides an easy way of producing a theanine derivative bound to sugar at high yield with ease.

BEST MODE FOR CARRYING OUT THE INVENTION

The present invention is directed to a theanine derivative, a preparation method thereof, and a use thereof for anti-acne treatment, where the theanine derivative is represented by the following formula 1 or 2:

[Formula 1]

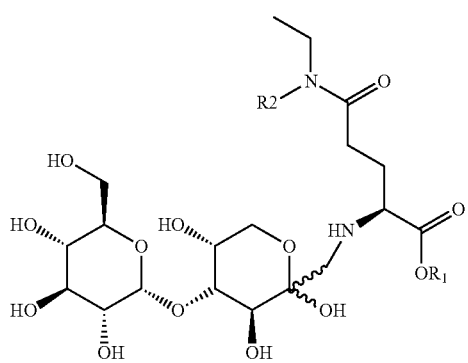

(In the formula, $R_1$ and $R_2$ are hydrogen, methyl, ethyl, propyl, isopropyl, n-butyl, isobutyl, or t-butyl),

[Formula 2]

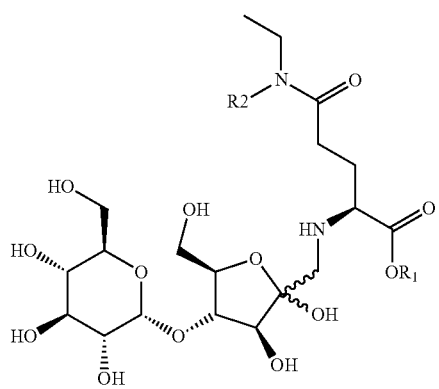

(In the formula, $R_1$ and $R_2$ are hydrogen, methyl, ethyl, propyl, isopropyl, n-butyl, isobutyl, or t-butyl).

Hereinafter, the present invention will be described in further detail.

The method for preparing a theanine derivative of the formula 1 or 2 according to the present invention comprises: heating the following compound A and maltose in a reaction solvent under agitation to activate a reaction; and precipitating a product in the reaction solvent, and can be illustrated as the following reaction scheme 1:

[Reaction Scheme 1]

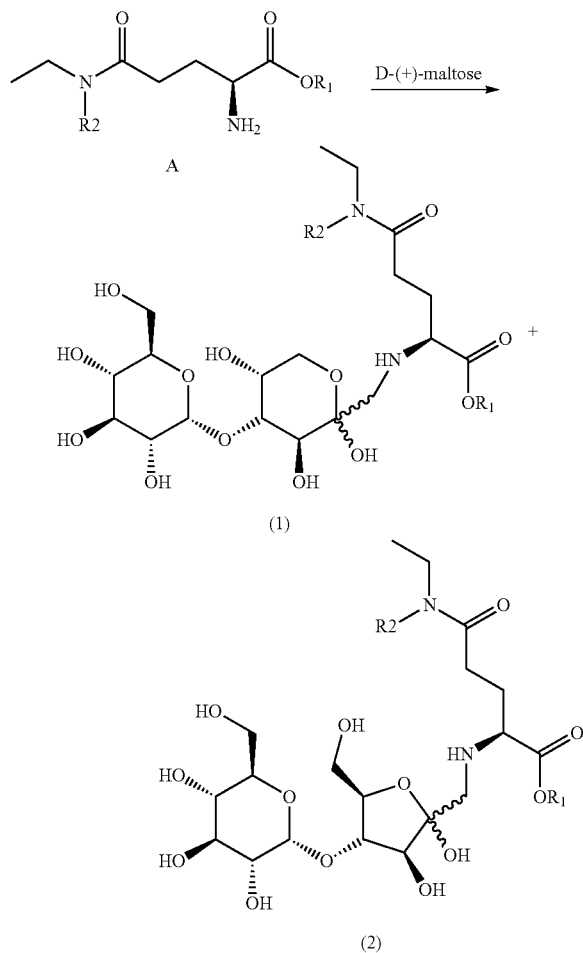

In the formulas, $R_1$ and $R_2$ are hydrogen, methyl, ethyl, propyl, isopropyl, n-butyl, isobutyl, or t-butyl.

Hereinafter, the method for preparing a theanine derivative of the formula 1 or 2 according to the present invention will be described in further detail.

(1) Step of Heating the Compound a and Maltose in a Reaction Solvent Under Agitation to Activate a Reaction.

The compound A and maltose are preferably mixed together at a molar ratio of 0.8:1 to 1.2:1. A molar ratio of less than 0.8:1 results in difficult of purification using recrystallization due to the presence of unreacted maltose, thereby needing an additional purification step, whereas a molar ratio of greater than 1.2:1 unnecessarily leaves the unreacted compound A, deteriorating the economic feasibility and undesirably making it difficult to purify the product by recrystallization.

It is of importance to select an appropriate reaction solvent to naturally precipitate the product in the reaction solvent with the progress of the reaction of the compound A and maltose as heated under agitation. The precipitation of the product in the reaction solvent can minimize potential side reactions, induce the equilibrium of the reaction towards the product to increase the yield, and makes it easier to purify the desired product by isolation through recrystallization after the reaction.

The reaction solvent as used herein may include any one selected from the group consisting of water, methanol, n-propanol, isopropanol, n-butanol, isobutanol, t-butanol, 1,2-propanediol, 1,3-propanediol, 1,3-butanediol, and glycerol; or a mixture of at least two selected from the group consisting of water, methanol, ethanol, n-propanol, isopropanol, n-butanol, iso-butanol, t-butanol, 1,2-propanediol, 1,3-propanediol, 1,3-butanediol, and glycerol.

The reaction temperature of the reaction is preferably in the range of 60 to 70° C. The reaction temperature below 60° C. retards the reaction rate to prolong the reaction time, whereas the reaction temperature above 70° C. undesirably increases the side reactions.

The reaction time of the reaction is preferably in the range of 12 to 48 hours. The reaction time shorter than 12 hours makes the progress of the reaction incomplete, thus reducing the yield of the product, whereas the reaction time longer than 48 hours results in increased side reactions, thus reducing the yield of the product.

(2) Step of Precipitating a Product in the Reaction Solvent

Standing the reactant solution at the room temperature after the completion of the reaction results in precipitation of the product in the reaction solvent, and the filtration of the precipitate leaves a theanine derivative in the form of white solid powder.

The theanine derivative of the formula 1 or 2 as prepared according to the present invention is present in the form of a mixture in equilibrium as mixed at the ratio of 2:1 to 10:1.

The theanine derivative of the present invention can be contained in a composition for topical application or a cosmetic composition as an effective ingredient.

The theanine derivative of the present invention can be contained in a composition for topical application in an effective amount to achieve an anti-acne efficacy. In other words, the content of the theanine derivative in the composition for topical application is preferably in the range of 0.001 to 20.0 wt %, more preferably 0.01 to 5 wt % with respect to the total weight of the composition. The content of the theanine derivative less than 0.001 wt % cannot achieve a desired efficacy, whereas the content of the theanine derivative greater than 20.0 wt % results in potential deformation of the composition, difficulty of controlling the viscosity of the formulation, and reduced economic feasibility for the product.

The composition for topical application or the cosmetic composition of the present invention may be formulated using a cosmetically or dermatologically acceptable carrier or vehicle. The composition includes all types of formulations suitable for topical application, such as, for example, solution, gel, solid, paste anhydrous product, oil-in-water emulsion, suspension, miéo-emulsion, microcapsules, microgranules, ionic (liposome) and nonionic vesicle dispersant, cream, skin toner, lotion, powder, ointment, spray, massage pack, or concealer. Alternatively, the composition may be used in the form of a foamed composition or an aerosol composition further containing a compressed propellant. These compositions can be prepared according to the typical methods known to those skilled in the art.

Further, the composition for topical application or the cosmetic composition of the present invention may contain adjuvants typically used in the cosmetic or dermatological fields, such as fat matters, organic solvents, solubilizers, concentrating agents, gelating agents, softening agents, antioxidants, suspending agents, stabilizers, foaming agents, fragrance, surfactants, water, ionic or nonionic emulsifying agents, fillers, sequestering agents, chelating agents, preservatives, vitamins, blocking agents, wetting agents, essential oils, dyes, pigments, hydrophilic or hydrophobic activators, lipid vesicles, or other ingredients typically used in cosmetics. The adjuvants may be used in an amount typically acceptable in the cosmetic or dermatological fields.

Further, the composition of the present invention may further contain other existing anti-acne components than the theanine derivative for the sake of providing anti-acne efficacies. The types and content of the existing anti-acne components are known to those skilled in the art.

The formulation of the cosmetic composition of the present invention is not specifically limited and may include, for example, skin toner, emulsion, massage cream, nutrient cream, massage pack, gel, or skin patch type cosmetics.

Hereinafter, the composition and effects of the present invention will be described with reference to the experiment examples and examples, which are given only for better understandings of the present invention and intended not to limit the scope of the present invention.

EXAMPLE 1

Maltulosyl Theanine 8.7 g (50 mmol) of theanine and 19.3 g (53.6 mmol) of maltose were added in 130 ml of methanol and refluxed at 65° C. for 18 hours. After the completion of the reaction, the mixture was kept at the room temperature for 3 hours and subjected to filtration to obtain a mixture of maltulosyl theanine represented by the following formula 3 or 4 (12.9 g, 52% yield) as a white powder.

$^1$H NMR (D$_2$O, δ): 5.24 (1H), 4.20 (1H), 4.07 (1H), 3.99 (2H), 3.79 (7H), 3.57 (1H), 3.43 (1H), 3.33 (1H), 3.20 (2H), 2.46 (2H), 2.17 (2H), 1.11 (3H) (Peaks are shown for major compounds only.)

LC-Mass: 499 [M+H]

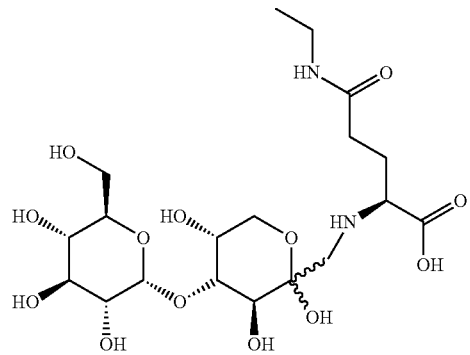

[Formula 3]

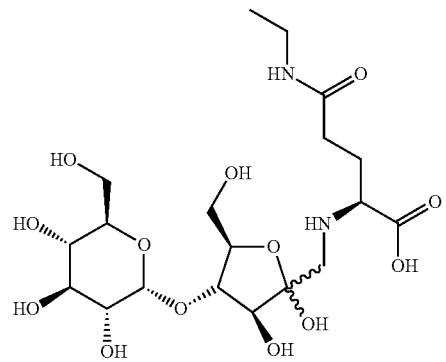

[Formula 4]

COMPARATIVE EXAMPLE 1

Maltulosyl Theanine

The procedures were performed in the same manner as described in example 1, excepting that ethanol was used as a solvent from which the product was not naturally precipitated. Ion-exchange resin chromatography rather than recrystallization was used to obtain the final product, maltulosyl theanine as a yellowish powder (8.0 g, 32% yield).

Comparative example 1 increased side reactions to result in lower yield of the product than example 1 and had the desired product in a different color due to the effect of by-products.

EXAMPLE 2

Maltulosyl Theanine Methyl Ester 9.4 g (50 mmol) of methyl ester theanine and 19.3 g (53.6 mmol) of maltose were added in 130 ml of a mixture solution (methanol:isopropanol=4:1) and refluxed at 65° C. for 18 hours. After the completion of the reaction, the mixture was kept at the room temperature for 3 hours and subjected to filtration to obtain a mixture of maltulosyl theanine methyl ester represented by the following formula 5 or 6 (14.3 g, 56% yield) as a white powder.

$^1$H NMR (D$_2$O, δ): 5.24 (1H), 4.19 (1H), 4.07 (1H), 4.00 (2H), 3.77 (10H), 3.57 (1H), 3.43 (1H), 3.33 (1H), 3.20 (2H), 2.46 (2H), 2.16 (2H), 1.11 (3H) (Peaks are shown for major compounds only.)

LC-Mass: 513 [M+H]

[Formula 5]

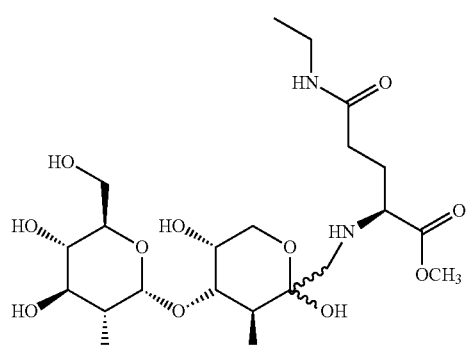

[Formula 6]

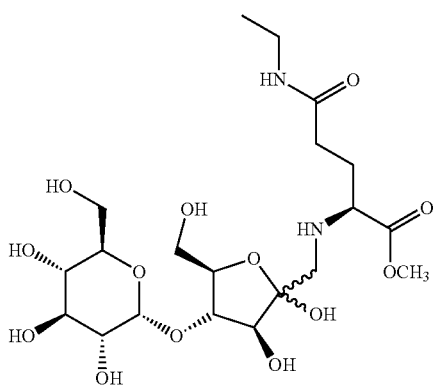

EXAMPLE 3

Maltulosyl N-Ethyl Theanine 10.1 g (50 mmol) of N-ethyl theanine and 19.3 g (53.6 mmol) of maltose were added in 130 ml of a mixture solution (methanol:ethanol=4:1) and refluxed at 65° C. for 18 hours. After the completion of the reaction, the mixture was kept at the room temperature for 3 hours and subjected to filtration to obtain a mixture of maltulosyl N-ethyl theanine represented by the following formula 7 or 8 (12.1 g, 46% yield) as a white powder.

$^1$H NMR (D$_2$O, δ): 5.26 (1H), 4.20 (1H), 4.06 (1H), 3.99 (2H), 3.81 (7H), 3.54 (1H), 3.43 (1H), 3.33 (1H), 3.25 (4H), 2.46 (2H), 2.19 (2H), 1.11 (3H), 1.05 (3H) (Peaks are shown for major compounds only.)

LC-Mass: 527 [M+H]

[Formula 7]

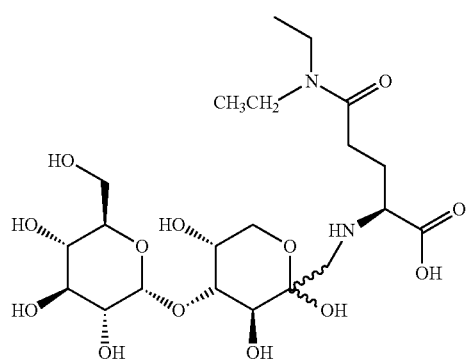

[Formula 8]

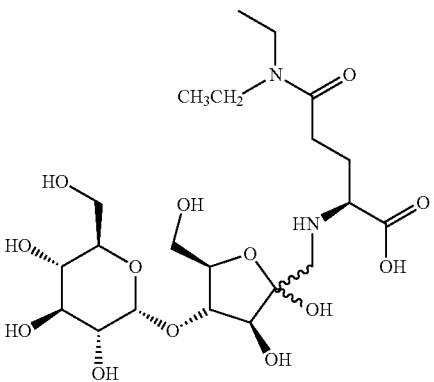

EXPERIMENT EXAMPLE 1

Selective Anti-Acne Effect on *P. acnes*

Each sample was added to an aqueous solution of 1% peptone and sterilized. 20 µl/ml of a test germ solution was injected into the sample-containing sterilized aqueous solution of peptone and then subjected to shaking culture at 32° C. for one day. The test germs selected were *P. acnes* known as present in the skin and harmful to the skin and *S. Epidermidis* known as relatively harmless to the skin. The solution after the shaking culture was diluted to 1/100 with normal diluting water. 0.1 ml of the diluted solution was placed on a Petri dish and then sterilized. To the diluted solution was poured TS agar cooled down to about 50° C. The Petri dish hardened with the TS agar was subjected to anaerobic culture at 35° C. for one day to measure the count of the germs. The *P. acnes* group was subjected to anaerobic culture at 35° C. for one day and then diluted to 1/100 with normal diluting water. 0.1 ml of the diluted solution was placed on a Petri dish, hardened with BHI agar, and subjected to anaerobic culture at 35° C. for 3 days to count the germs. As comparative groups, theanine and maltose were used for the testing. The count of germs in the control group without containing the sample was defined as 100%. The experimental results are presented in Table 1.

TABLE 1

| Div. | S. Epidermidis (%) | P. acnes (%) |
| --- | --- | --- |
| Control | 100 | 100 |
| Theanine | 98 | 50 |
| Maltose | 89 | 110 |
| Example 1 | 83 | 9 |
| Example 2 | 93 | 27 |
| Example 3 | 86 | 15 |

As can be seen from Table 1, unlike theanine or maltose, the theanine derivatives of examples 1, 2 and 3 had no significant change in the count of S. Epidermidis and a reduced count of *P. acnes* to the significant level. This demonstrates that the introduction of sugar into theanine increased the selective anti-acne effect on *P. acnes*.

Accordingly, the theanine derivative of the present invention proved to have a selective and good anti-acne effect on *P. acnes* without affecting the germs present in the skin but not significantly harmful to the skin.

EXPERIMENT EXAMPLE 2

Primary Skin Irritation Test

An aqueous solution of each theanine derivative of examples 1, 2 and 3 was applied on the lower part of the arm of 20 healthy male and female subjects according to the closed patch test method. The arm was covered with a plastic cap to block external stimuli. After one day, the skin irritation was observed and evaluated according to the evaluation method shown in Table 2. The results are presented in Table 3. All numeral designations in Table 3 are averages of the irritations calculated according to the evaluation method of Table 2.

TABLE 2

| Evaluation Number | Extent of Skin Irritation |
|---|---|
| 0 | None |
| 1 | Minimum |
| 2 | Slight (red spots) |
| 3 | Severe (red spots, swelling) |
| 4 | Extreme (red spots, swelling) |

TABLE 3

| Div. | Extent of Skin Irritation |
|---|---|
| Example 1 | 0.1 |
| Example 2 | 0.2 |
| Example 3 | 0.1 |

As can be seen from Table 3, the theanine derivatives of examples 1, 2 and 3 proved to be safe to the skin, causing little irritations on the skin.

EXPERIMENT EXAMPLE 3

Anti-Acne Effect Testing

Formulation examples 1, 2, and 3 containing the theanine derivatives of Examples 1, 2, and 3, respectively, and comparative formulation example 1 containing none of the theanine derivatives were prepared according to the compositions shown in Table 4 (unit: wt %).

For 4 weeks, each of the formulation examples 1, 2, and 3 and the comparative formulation example 1 was applied to 20 male patients (19 to 26 years old) with acnes in the same manner of applying a normal skin toner. The improvement of acnes was evaluated as determined by the opinions of the patients according to the following evaluation standards. The results are presented in Table 5.

TABLE 4

| Ingredients | Formulation Example 1 | Formulation Example 2 | Formulation Example 3 | Comparative Formulation Example 1 |
|---|---|---|---|---|
| Purified water | To 100 | To 100 | To 100 | To 100 |
| Glycerin | 8.0 | 8.0 | 8.0 | 8.0 |
| Butylene glycol | 4.0 | 4.0 | 4.0 | 4.0 |
| Hyaluronic acid extract | 5.0 | 5.0 | 5.0 | 5.0 |
| β-glucan | 7.0 | 7.0 | 7.0 | 7.0 |
| Carbomer | 0.1 | 0.1 | 0.1 | 0.1 |
| Example 1 | 1.0 | — | — | — |
| Example 2 | — | 1.0 | — | — |
| Example 3 | — | — | 1.0 | — |
| Caprylic/capric triglyceride | 8.0 | 8.0 | 8.0 | 8.0 |
| Squalane | 5.0 | 5.0 | 5.0 | 5.0 |
| Stearyl glucoside | 1.5 | 1.5 | 1.5 | 1.5 |
| Sorbitan stearate | 0.4 | 0.4 | 0.4 | 0.4 |
| Stearyl alcohol | 1.0 | 1.0 | 1.0 | 1.0 |
| Preservative | q.s. | q.s. | q.s. | q.s. |
| Fragrance | q.s. | q.s. | q.s. | q.s. |
| Colorant | q.s. | q.s. | q.s. | q.s. |
| Triethanol amine | 0.1 | 0.1 | 0.1 | 0.1 |

TABLE 5

| Div. | Evaluation of Anti-acne Effect | | | |
|---|---|---|---|---|
| | 1 week | 2 weeks | 3 weeks | 4 weeks |
| Formulation Example 1 | + | + | ++ | +++ |
| Formulation Example 2 | ± | + | + | ++ |
| Formulation Example 3 | + | + | ++ | ++ |
| Comparative Formulation Example 1 | ± | ± | ± | ± |

<Evaluation Standards>
+++: Very much improved
++: Considerably improved
+: Slightly improved
±: Neither improved nor worsened
−: worsened without improvement As can be seen from Table 5, the formulation examples 1, 2 and 3 containing the theanine derivatives of the present invention had an anti-acne effect faster and stronger than the comparative formulation example 1 containing none of the theanine derivatives.

FORMULATION EXAMPLE 4

Nutrient Lotion (Milk Lotion)

A nutrient lotion formulation containing the theanine derivatives of examples 1, 2 and 3 was prepared according to the following composition.

TABLE 6

| Ingredients | Content (wt %) |
|---|---|
| Purified water | To 100 |
| Glycerin | 8.0 |
| Butylene glycol | 4.0 |
| Hyaluronic acid extract | 5.0 |
| β-glucan | 7.0 |
| Carbomer | 0.1 |
| Theanine derivative (at least one of Examples 1, 2 and 3) | 0.05 |
| Caprylic/capric triglyceride | 8.0 |
| Squalane | 5.0 |
| Stearyl glucoside | 1.5 |
| Sorbitan stearate | 0.4 |
| Stearyl alcohol | 1.0 |
| Preservative | q.s. |
| Fragrance | q.s. |
| Colorant | q.s. |
| Triethanol amine | 0.1 |

FORMULATION EXAMPLE 5

Nutrient Cream

A nutrient cream formulation containing the theanine derivatives of examples 1, 2 and 3 was prepared according to the following composition.

TABLE 7

| Ingredients | Content (wt %) |
|---|---|
| Purified water | To 100 |
| Glycerin | 3.0 |
| Butylene glycol | 3.0 |
| Liquid paraffin | 7.0 |
| β-glucan | 7.0 |
| Carbomer | 0.1 |
| Theanine derivative (at least one of examples 1, 2 and 3) | 0.05 |
| Caprylic/capric triglyceride | 3.0 |
| Squalane | 5.0 |
| Stearyl glucoside | 1.5 |
| Sorbitan stearate | 0.4 |
| Polysorbate | 1.2 |
| Preservative | q.s. |
| Fragrance | q.s. |
| Colorant | q.s. |
| Triethanol amine | 0.1 |

FORMULATION EXAMPLE 6

Massage Cream

A massage cream formulation containing the theanine derivatives of examples 1, 2 and 3 was prepared according to the following composition.

TABLE 8

| Ingredients | Content (wt %) |
|---|---|
| Purified water | To 100 |
| Glycerin | 8.0 |
| Butylene glycol | 4.0 |
| Liquid paraffin | 45.0 |
| β-glucan | 7.0 |
| Carbomer | 0.1 |
| Theanine derivative (at least one of examples 1, 2 and 3) | 0.05 |
| Caprylic/capric triglyceride | 3.0 |
| Wax | 4.0 |
| Stearyl glucoside | 1.5 |
| Sorbitan sesquioleate | 0.9 |
| Vaseline | 3.0 |
| Preservative | q.s. |
| Fragrance | q.s. |
| Colorant | q.s. |
| Paraffin | 1.5 |

FORMULATION EXAMPLE 7

Ointment

An ointment formulation containing the theanine derivatives of examples 1, 2 and 3 was prepared according to the following composition.

TABLE 9

| Ingredients | Content (wt %) |
|---|---|
| Purified water | To 100 |
| Glycerin | 8.0 |
| Butylene glycol | 4.0 |
| Liquid paraffin | 15.0 |
| β-glucan | 7.0 |
| Carbomer | 0.1 |
| Theanine derivative (at least one of examples 1, 2 and 3) | 0.05 |
| Caprylic/capric triglyceride | 3.0 |
| Squalane | 1.0 |
| Stearyl glucoside | 1.5 |
| Sorbitan stearate | 0.4 |
| Stearyl alcohol | 1.0 |
| Preservative | q.s. |
| Fragrance | q.s. |
| Colorant | q.s. |
| Wax | 4.0 |

The invention claimed is:

1. A theanine derivative represented by the following formula 1 or 2:

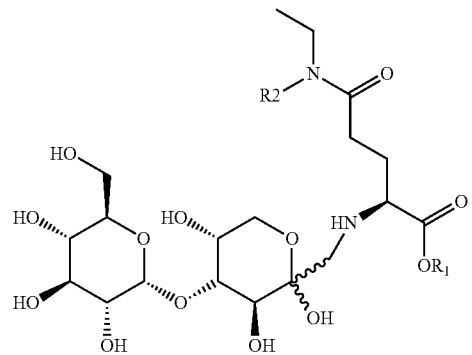

Formula 1 wherein $R_1$ and $R_2$ are each hydrogen, methyl, ethyl, propyl, isopropyl, n-butyl, isobutyl, or t-butyl,

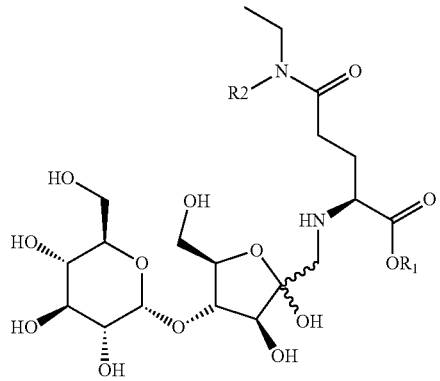

Formula 2 wherein $R_1$ and $R_2$ are each hydrogen, methyl, ethyl, propyl, isopropyl, n-butyl, isobutyl, or t-butyl.

2. A method of the topical treatment of acne in a subject having acne comprising topically applying an effective amount of the theanine derivative as claimed in claim 1.

3. A composition for topical application for anti-acne treatment containing the theanine derivative as claimed in claim 1 as an effective ingredient.

4. The composition for topical application for anti-acne treatment as claimed in claim 3, wherein the composition for topical application contains 0.001 to 20.0 wt % of the theanine derivative with respect to the total weight of the composition.

5. A cosmetic composition containing the theanine derivative as claimed in claim 1 as an effective ingredient and a dermatologically acceptable carrier.

6. The cosmetic composition as claimed in claim 5, wherein the cosmetic composition contains 0.001 to 20.0 wt % of the theanine derivative with respect to the total weight of the composition.

7. A method for preparing a theanine derivative represented by the following formula (1) or (2):

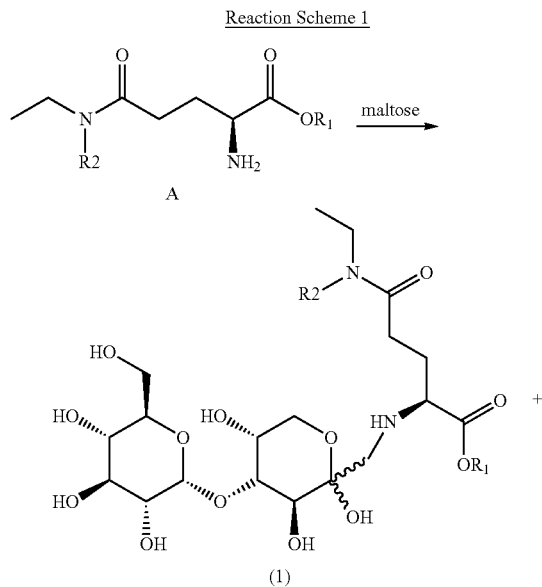

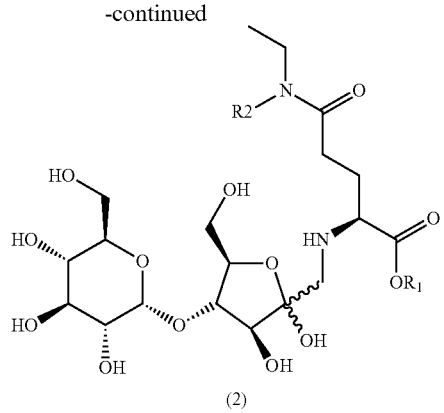

wherein $R_1$ and $R_2$ are hydrogen, methyl, ethyl, propyl, isopropyl, n-butyl, isobutyl, or t-butyl, the method comprising:

heating the compound A and maltose in a reaction solvent under agitation to activate a reaction; and precipitating a product in the reaction solvent.

8. The method as claimed in claim 7, wherein the compound A and maltose are mixed together at a molar ratio of 0.8:1 to 1.2:1.

9. The method as claimed in claim 7, wherein the reaction solvent comprises any one selected from the group consisting of water, methanol, n-propanol, isopropanol, n-butanol, isobutanol, t-butanol, 1,2-propanediol, 1,3-propanediol, 1,3-butanediol, and glycerol; or a mixture of at least two selected from the group consisting of water, methanol, ethanol, n-propanol, isopropanol, n-butanol, iso-butanol, t-butanol, 1,2-propanediol, 1,3-propanediol, 1,3-butanediol, and glycerol.

10. The method as claimed in claim 7, wherein the reaction temperature is 60 to 70° C.

\* \* \* \* \*